(12) United States Patent
Morgan et al.

(10) Patent No.: US 7,955,296 B1
(45) Date of Patent: Jun. 7, 2011

(54) BIOLOGICALLY ENHANCED IRRIGANTS

(75) Inventors: Roy E. Morgan, San Jose, CA (US); Wayne K. Augé, II, Santa Fe, CA (US)

(73) Assignee: NuOrtho Surgical, Inc., Fall River, MA (US)

( * ) Notice: Subject to any disclaimer, the term of this patent is extended or adjusted under 35 U.S.C. 154(b) by 412 days.

(21) Appl. No.: 11/444,724

(22) Filed: Jun. 1, 2006

Related U.S. Application Data

(62) Division of application No. 10/157,651, filed on May 28, 2002, now Pat. No. 7,066,932.

(60) Provisional application No. 60/293,809, filed on May 26, 2001.

(51) Int. Cl.
*A61M 31/00* (2006.01)

(52) U.S. Cl. ........................... 604/48; 604/19

(58) Field of Classification Search ............ 604/19, 604/27, 48
See application file for complete search history.

(56) References Cited

U.S. PATENT DOCUMENTS

| | | | |
|---|---|---|---|
| 3,911,107 A * | 10/1975 | Krezanoski | 424/667 |
| 3,941,135 A | 3/1976 | von Sturm et al. | |
| 3,982,017 A | 9/1976 | Thiele | |
| 4,014,777 A | 3/1977 | Brown | |
| 4,105,017 A | 8/1978 | Ryaby et al. | |
| 4,266,532 A | 5/1981 | Ryaby et al. | |
| 4,266,533 A | 5/1981 | Ryaby et al. | |
| 4,504,493 A * | 3/1985 | Marshall et al. | 514/738 |
| 4,540,409 A | 9/1985 | Nystrom et al. | |
| 4,615,347 A | 10/1986 | Schooley | |
| 4,872,865 A | 10/1989 | Bloebaum et al. | |
| 4,938,970 A | 7/1990 | Hustead et al. | |
| 4,971,068 A | 11/1990 | Sahi | |
| 5,014,699 A | 5/1991 | Pollack et al. | |
| 5,236,456 A | 8/1993 | O'Leary et al. | |
| 5,282,861 A | 2/1994 | Kaplan | |
| 5,304,724 A | 4/1994 | Newton | |
| 5,314,476 A | 5/1994 | Prewett et al. | |
| 5,352,463 A | 10/1994 | Badylak et al. | |
| 5,360,440 A | 11/1994 | Andersen | |
| 5,366,443 A | 11/1994 | Eggers et al. | |
| 5,403,825 A | 4/1995 | Lagarde et al. | |
| 5,458,596 A | 10/1995 | Lax et al. | |

(Continued)

FOREIGN PATENT DOCUMENTS

GB 2037920 7/1980

(Continued)

OTHER PUBLICATIONS

Babincova, Melina 1 "High-Gradient Magnetic Capture of Ferrofluids: Implications for Drug Targeting and Tumor Embolization", *Zeitschrift fur Naturforschung*, vol. 56-C 2001, 909-911.

Brennetor, R 1 "Investigation of Chelate Formation, Intramoecular Energy Transfer and Luminesecence Efficiency and Lifetimes in the Euthenoyltrifluoroacetone-triocylphosphine oxide-Triton x-100 System of Using Absorbance, Fluorescence and Photothermal Measurements", *Spectrochim Acta A Mol. Biomol. Spectroscopy*, Part A-56 2000, 703-715.

(Continued)

*Primary Examiner* — Nicholas D Lucchesi
*Assistant Examiner* — Laura A Bouchelle
(74) *Attorney, Agent, or Firm* — Janeen Vilven; Vidal A. Oaxaca; Peacock Myers, P.C.

(57) ABSTRACT

Compositions, systems and methods utilizing engineered surgical irrigants providing delivery of components with therapeutic or other secondary benefits. Engineered irrigants provide targeted delivery of desired agents, including agents for propulsion of nano-devices, agents including molecular probes, gene expression agents, magnetically orientable agents, agents for discrete tissue temperature detection and tissue regeneration agents.

1 Claim, 13 Drawing Sheets

U.S. PATENT DOCUMENTS

| | | | |
|---|---|---|---|
| 5,494,538 A | 2/1996 | Kirillov et al. | |
| 5,498,259 A | 3/1996 | Mourant et al. | |
| 5,514,130 A | 5/1996 | Baker | |
| 5,516,533 A | 5/1996 | Badylak et al. | |
| 5,554,141 A | 9/1996 | Wendler | |
| 5,569,242 A | 10/1996 | Lax et al. | |
| 5,584,863 A | 12/1996 | Rauch et al. | |
| 5,622,725 A * | 4/1997 | Kross | 424/665 |
| 5,669,904 A | 9/1997 | Platt et al. | |
| 5,669,907 A | 9/1997 | Platt et al. | |
| 5,669,934 A | 9/1997 | Sawyer | |
| 5,683,366 A | 11/1997 | Eggers et al. | |
| 5,697,281 A | 12/1997 | Eggers et al. | |
| 5,697,536 A | 12/1997 | Eggers et al. | |
| 5,697,882 A | 12/1997 | Eggers et al. | |
| 5,697,909 A | 12/1997 | Eggers et al. | |
| 5,741,261 A | 4/1998 | Moskovitz et al. | |
| 5,746,896 A | 5/1998 | Shimamune et al. | |
| 5,749,895 A | 5/1998 | Sawyer et al. | |
| 5,788,976 A | 8/1998 | Bradford | |
| 5,800,385 A | 9/1998 | Demopulos et al. | |
| 5,820,583 A | 10/1998 | Demopulos et al. | |
| 5,824,015 A | 10/1998 | Sawyer | |
| 5,840,166 A | 11/1998 | Kaneko | |
| 5,855,608 A | 1/1999 | Brekke et al. | |
| 5,860,950 A | 1/1999 | Demopulos et al. | |
| 5,871,469 A | 2/1999 | Eggers et al. | |
| 5,885,292 A | 3/1999 | Moskovitz et al. | |
| 5,919,191 A | 7/1999 | Lennox et al. | |
| 5,955,514 A | 9/1999 | Huang et al. | |
| 5,964,968 A | 10/1999 | Kaneko | |
| 6,032,077 A | 2/2000 | Pomeranz | |
| 6,033,654 A | 3/2000 | Stedronsky et al. | |
| 6,086,585 A | 7/2000 | Hovda et al. | |
| 6,112,122 A | 8/2000 | Schwardt et al. | |
| 6,117,109 A | 9/2000 | Eggers et al. | |
| 6,135,998 A | 10/2000 | Palanker | |
| 6,149,620 A | 11/2000 | Baker et al. | |
| 6,159,194 A | 12/2000 | Eggers et al. | |
| 6,162,219 A | 12/2000 | Nilsson et al. | |
| 6,174,309 B1 | 1/2001 | Wrublewski et al. | |
| 6,206,878 B1 | 3/2001 | Bishop et al. | |
| 6,207,134 B1 * | 3/2001 | Fahlvik et al. | 424/9.322 |
| 6,213,999 B1 | 4/2001 | Platt et al. | |
| 6,214,003 B1 | 4/2001 | Morgan et al. | |
| 6,224,592 B1 | 5/2001 | Eggers et al. | |
| 6,235,024 B1 | 5/2001 | Tu | |
| 6,241,723 B1 | 6/2001 | Heim et al. | |
| 6,241,753 B1 | 6/2001 | Knowlton | |
| 6,264,650 B1 | 7/2001 | Hovda et al. | |
| 6,264,652 B1 | 7/2001 | Eggers et al. | |
| 6,273,883 B1 | 8/2001 | Furumoto | |
| 6,293,942 B1 | 9/2001 | Goble et al. | |
| 6,306,134 B1 | 10/2001 | Goble et al. | |
| 6,309,387 B1 | 10/2001 | Eggers et al. | |
| 6,322,549 B1 | 11/2001 | Eggers et al. | |
| 6,350,276 B1 | 2/2002 | Knowlton | |
| 6,383,184 B1 | 5/2002 | Sharkey | |
| 6,391,025 B1 | 5/2002 | Weinstein et al. | |
| 6,416,509 B1 * | 7/2002 | Goble et al. | 606/37 |
| 6,419,815 B1 | 7/2002 | Chambers et al. | |
| 6,461,352 B2 | 10/2002 | Morgan et al. | |
| 6,463,336 B1 | 10/2002 | Mawhinney | |
| 6,471,993 B1 | 10/2002 | Shastri et al. | |
| 6,547,794 B2 | 4/2003 | Auge | |
| 6,558,382 B2 | 5/2003 | Jahns et al. | |
| 6,772,013 B1 | 8/2004 | Ingle et al. | |
| 6,780,178 B2 | 8/2004 | Palanker et al. | |
| 6,824,555 B1 | 11/2004 | Towler et al. | |
| 6,832,995 B1 | 12/2004 | Towler et al. | |
| 6,890,332 B2 | 5/2005 | Truckai et al. | |
| 6,902,564 B2 | 6/2005 | Morgan et al. | |
| 7,066,932 B1 | 6/2006 | Morgan et al. | |
| 7,105,011 B2 | 9/2006 | Auge | |
| 7,354,438 B2 | 4/2008 | Morgan et al. | |
| 7,445,619 B2 | 11/2008 | Auge et al. | |
| 7,549,989 B2 | 6/2009 | Morgan et al. | |
| 2001/0007940 A1 | 7/2001 | Tu et al. | |
| 2002/0165596 A1 | 11/2002 | Wilson | |
| 2003/0028189 A1 | 2/2003 | Woloszko et al. | |
| 2003/0216732 A1 | 11/2003 | Truckai et al. | |
| 2003/0216733 A1 | 11/2003 | McClurken et al. | |
| 2004/0167244 A1 | 8/2004 | Auge, II | |
| 2004/0267255 A1 | 12/2004 | Auge, II et al. | |
| 2005/0085806 A1 | 4/2005 | Auge, II et al. | |
| 2005/0182449 A1 | 8/2005 | Auge, II et al. | |
| 2009/0030410 A1 | 1/2009 | Auge, II et al. | |
| 2009/0306645 A1 | 12/2009 | Morgan et al. | |

FOREIGN PATENT DOCUMENTS

| | | |
|---|---|---|
| WO | WO02/102438 | 12/2002 |
| WO | WO03/015865 | 2/2003 |
| WO | WO03/103521 | 12/2003 |

OTHER PUBLICATIONS

Grant, Kyle M. "Magnetic Field-Controlled Microfluidic Transport", *Journal of American Chemical Society (JACS) Articles*, vol. 124, No. 3 2002, 462-467.

Minczykowski, Andrzej "Effects of Magnetic Resonance Imaging on Polymorphonuclear Neutrophil Adhesion", *Diagnostics and Medical Technolgy, Medical Science Monitor*, vol. 7(3) 2001, 482-488.

Torchilin, Vladimir P. "Drug Targeting", *European Journal of Pharmaceutical Sciences*, vol. 11, Supplemental 2 2000, S81-S91.

Zohar, Ofer "Thermal Imaging of Reeptor-Activated Heat Production in Single Cells", *Biophysical Journal*, vol. 74 Jan. 1998, 82-89.

Chen, S. S. et al., "Heat-Induced Changes in the Mechanics of a Collagenous Tissue: Isothermal, Isotonic Shrinkage", *Transactions of the ASME* vol. 120 1998, 382-388.

Edwards, R B. et al., "Thermometric determination of cartilage matrix temperatures during thermal chondroplasty: comparison of bipolar and monopolar radiofrequency devices", *Arthroscopy* Apr. 2002;18(4) Apr. 2002, 339-346.

Fink, Bernd et al., "Holmium: YAG Laser-Induced Aseptic Bone Necroses of the Femoral Condyle", *Arthroscopy: The Journal of Arthroscopic and Related Surgery* vol. 12 No. 2, 1996, 217-223.

Gould, Stephen E. et al., "Cellular Contribution of Bone Graft to Fusion", *Journal of Orthopaedic Research* vol. 18 2000, 920-927.

Ito, Takayasu et al., "Sensitivity of Osteoinductive Activity of Deminerlization and Defatted Rat Femur to Temperature and Duration of Heating", *Clinical Orthopaedics and Related Research Research* No. 316 1995, 267-275.

Janzen, Dennis L. et al., "Osteonecrosis After Contact Neodymium: Yttrium Aluminum Garnet Arthroscopic Laser Meniscectomy", *AJR* 169 1997, 855-858.

Lopez, Mandi J. et al., "Effects of Monopolar Radiofrequency Energy on Ovine Joint Capsular Mechanical Properties", *Clinical Orthopaedics and Related Research*, No. 374 2000, 286-297.

Medvecky, Michael J. et al., "Thermal Capsular Shrinkage: Basic Science and Clinical Applications", *Arthroscopy*, 2001, vol. 17, No. 6 Jul. 2001, 624-635.

Rozbruch, S. R. et al., "Osteonecrosis of the Knee Following Arthroscopic Laser Meniscectomy", *Arthroscopy: The Journal of Arthroscopic and Related Surgery* vol. 12 No. 2 1996, 245-250.

Thal, Raymond et al., "Delayed Articular Cartilage Slough: Two Cases Resulting From Holmium: YAG Laser Damage to Normal Articular Cartilage and a Review of the Literature", *Arthroscopy: The Journal of Arthroscopic and Related Surgery* vol. 12 No. 1 1996, 92-94.

Wall, Michael S. et al., "Thermal Modification of Collagen", *J. Shoulder Elbow Surg.* vol. 8 No. 4 1999, 339-344.

Wallace, Andrew L. et al., "Electrothermal Shrinkage Reduces Laxity but Alters Creep Behavior in a Lapine Ligament Model", *J. Shoulder Elbow Surg.* vol. 10 No. 1 2001, 1-6.

Zhang, Min et al., ""Effects of the Demineralization Process on the Osteoinductivity of Demineralized Bone Matrix"", *J. Periodontaol*, vol. 68 No. 11 Nov. 1997, 1085-1092.

\* cited by examiner

BIOLOGICALLY ENHANCED IRRIGANTS

CROSS-REFERENCE TO RELATED APPLICATIONS

This application is a divisional application of U.S. patent application Ser. No. 10/157,651, titled Biologically Enhanced Irrigants, filed on May 28, 2002, and the specification and claims of that application are incorporated herein by reference.

This application claims the benefit of the filing of U.S. Provisional Patent Application Ser. No. 60/293,809, titled "System and Method of Biologically Enhanced Irrigants in Surgical Procedures," filed on May 26, 2001, and the specification of that application is incorporated herein by reference.

BACKGROUND OF THE INVENTION

1. Field of the Invention (Technical Field)

The present invention relates to the general field of surgical irrigants, and in particular biologically enhanced irrigant solutions. Irrigant solutions are provided that include biologically active chemical structures and fluids that attach, by any means, to specific tissue types, or that additionally or alternatively provide release of specific compounds, components or elements that enhance surgical tool performance. The elements described herein may be employed in any surgical procedure utilizing irrigation as a means of wetting tissue to help maintain viability, distension of a working space, enhance visualization, enhance surgical tool performance, provide tissue nutrients, or the like, including specifically surgical procedures involving the articular joints in which irrigants are used as a distension and visualization medium.

2. Background Art

Note that the following discussion refers to a number of publications by author(s) and year of publication, and that due to recent publication dates certain publications are not to be considered as prior art vis-a-vis the present invention. Discussion of such publications herein is given for more complete background and is not to be construed as an admission that such publications are prior art for patentability determination purposes.

To date surgical irrigants have primarily focused on providing a "lavage" mode of use. Fluids for such purposes have been selected from organically based solutions designed to minimize water extravasation in those instances where the fluid is used as distension medium. Hydrostatic pressure and osmotic pressure are typically balanced to prevent excess water absorption or loss by tissue. As a result, during endoscopic procedures, the dominant majority of fluids are aimed at providing a transparent medium for visualization. U.S. Pat. No. 4,504,493, to Marshall et al., discloses a solution composed of glycerol and water and that is non-cytotoxic, non-hemolytic, non-viscid, non-conductive and optically clear.

For arthroscopic surgery, irrigants are disclosed that are hypertonic solutions, such as the solution disclosed in U.S. Pat. No. 4,872,865 to Bloebaum et al. The aqueous solution of U.S. Pat. No. 4,872,865 contains ions of sodium, chlorine, potassium and calcium, and the solution may be employed as an irrigant in arthroscopic surgery to reduce the risk of swelling and injury of the synovial tissues, and as a therapeutic treatment for swelling and inflammation. This is done, in part, by establishing an osmotic gradient that will tend to cause water and water soluble inflammatory products to be drawn out of the cells and tissues.

Other irrigant solutions are also known that contain a variety of salts, including sodium, calcium, potassium or magnesium. Thus electrolyte solutions are known, such as Ringer's solution, a combination of sodium, calcium and potassium ions with sodium lactate, and a variety of balanced salt solutions, many of which employ buffering systems. Also known are other solutions, such as those containing glutathione, sodium bicarbonate, dextrose and the like. For example, U.S. Pat. No. 5,304,724 to Newton discloses a formulation for and method of making certain such solutions.

It is also known to employ a local anesthetic as a component of an electrolyte solution administered by irrigation, such as that disclosed in U.S. Pat. No. 4,938,970 to Hustead et al. In U.S. Pat. No. 4,938,970 a buffered electrolyte salt solution is provided, the electrolytes present at a concentration where they do not cause pain, and further optionally including one or more local anesthetics, such as lidocaine, medivacaine, bupivacaine and the like.

Other irrigation solutions are known that can be employed to both inhibit pain and inflammation. Thus, U.S. Pat. No. 5,820,583 to Demopulos et al. discloses a solution, such as saline or lactated Ringer's solution, that contains components such as a $serotonin_2$ antagonist, a $serotonin_3$ antagonist, a histamine antagonist, a serotonin agonist, a cyclooxygenase inhibitor, a $neurokinin_1$ antagonist, an ATP-sensitive potassium channel opener, a calcium channel antagonist, a $bradykinin_1$ antagonist, a $bradykinin_2$ antagonist and a µ-opioid agonist. The multiple components are in low concentrations, and are directed at local inhibition of mediators of pain, inflammation, spasm and restenosis in a physiologic electrolyte carrier fluid. In a related patent, U.S. Pat. No. 5,860,950 also to Demopulos et al., methods of inhibiting pain and inflammation during arthroscopic surgery procedures, by delivery of multiple components as described, are described and claimed.

Irrigant solutions are thus employed which have limited therapeutic benefit, principally the inhibition of pain, and secondarily the inhibition of inflammatory processes and responses. There is a need for systems and solutions that may be employed to effect more than a single therapeutic purpose, including irrigant solutions that provide for desired distension and clearing of visual fields, as in arthroscopic surgery, and that also provide a desired therapeutic benefit.

SUMMARY OF THE INVENTION

Disclosure of the Invention

In one embodiment, the invention provides a solution for use in irrigation of surgical sites, which solution includes an isotonic and buffered component and at least one engineered irrigant component. The engineered irrigant component can include a thermally responsive component, a magnetic field responsive component, or a chemotactic responsive component. A thermally responsive component optionally effects a color or fluorescence change in response to a temperature change. The magnetic field responsive component includes a magnetic, paramagnetic or super paramagnetic particle with nanosize dimensions. Where a magnetic field responsive component is a particle, a therapeutic agent may be bound to that particle. The therapeutic agent bound to the magnetic field responsive component particle can include a receptor-specific agent or a gene expression agent. A chemotactic responsive component can include a therapeutic agent bound to it. The therapeutic agent bound to the chemotactic responsive component can include a receptor-specific agent or a gene expression agent.

In another embodiment, the invention provides a method for sustaining nano-device function within an aqueous medium, the method including the steps of providing a nano-device utilizing one or more motive components, providing a solution containing one or more motive components, and immersing the nano-device in the solution, whereby the nano-device utilizes the motive component. The motive component can include a lubricant. The motive component can also include carbon dioxide in solution. The aqueous medium can be an irrigation solution.

In another embodiment, a method for determining the temperature of tissue structures under application of energy in an electrosurgery procedure is provided, the method including the steps of providing a surgical irrigant solution comprising at least one thermally responsive component, applying the surgical irrigant solution to the surgical site, and detecting a thermal change upon application of energy in an electrosurgery procedure conducted within the surgical irrigant solution. In this embodiment, the step of detecting a thermal change can include detecting a color change in the at least one thermally responsive component, or detecting a fluorescence change in the at least one thermally responsive component.

A primary object of the present invention is to provide engineered irrigants for use in surgical procedures, wherein the irrigant contains components that provide therapeutic or diagnostic benefits.

Another object of the present invention is to provide surgical irrigants that include a thermally responsive component, whereby the thermally responsive component effects a color or fluorescence change in response to a temperature change.

Another object of the present invention is to provide a magnetic field responsive component, whereby the magnetic field responsive component can be directed to desired anatomical features by means of a magnetic field.

Another object of the present invention is to provide a magnetic field responsive component that includes a magnetic, paramagnetic or super paramagnetic particle with nanosize dimensions.

Another object of the present invention is to provide a magnetic field responsive component that can be used as a carrier or transport device for a therapeutic agent.

Another object of the present invention is to provide surgical irrigants that are adjuncts to nano-devices, such as providing a source of lubricant designed to be employed with such nano-devices or a source of fuel designed to be employed with such nano-devices.

Another object of the present invention is to provide surgical irrigants that can be employed with electrosurgical devices employing oxy-hydro combustion reactions at the surgical site.

Other objects, advantages and novel features, and further scope of applicability of the present invention will be set forth in part in the detailed description to follow, taken in conjunction with the accompanying drawings, and in part will become apparent to those skilled in the art upon examination of the following, or may be learned by practice of the invention. The objects and advantages of the invention may be realized and attained by means of the instrumentalities and combinations particularly pointed out in the appended claims.

BRIEF DESCRIPTION OF THE DRAWINGS

The accompanying drawings, which are incorporated into and form a part of the specification, illustrate one or more embodiments of the present invention and, together with the description, serve to explain the principles of the invention. The drawings are only for the purpose of illustrating one or more preferred embodiments of the invention and are not to be construed as limiting the invention. In the drawings.

DESCRIPTION OF THE PREFERRED EMBODIMENTS

Figure 1:
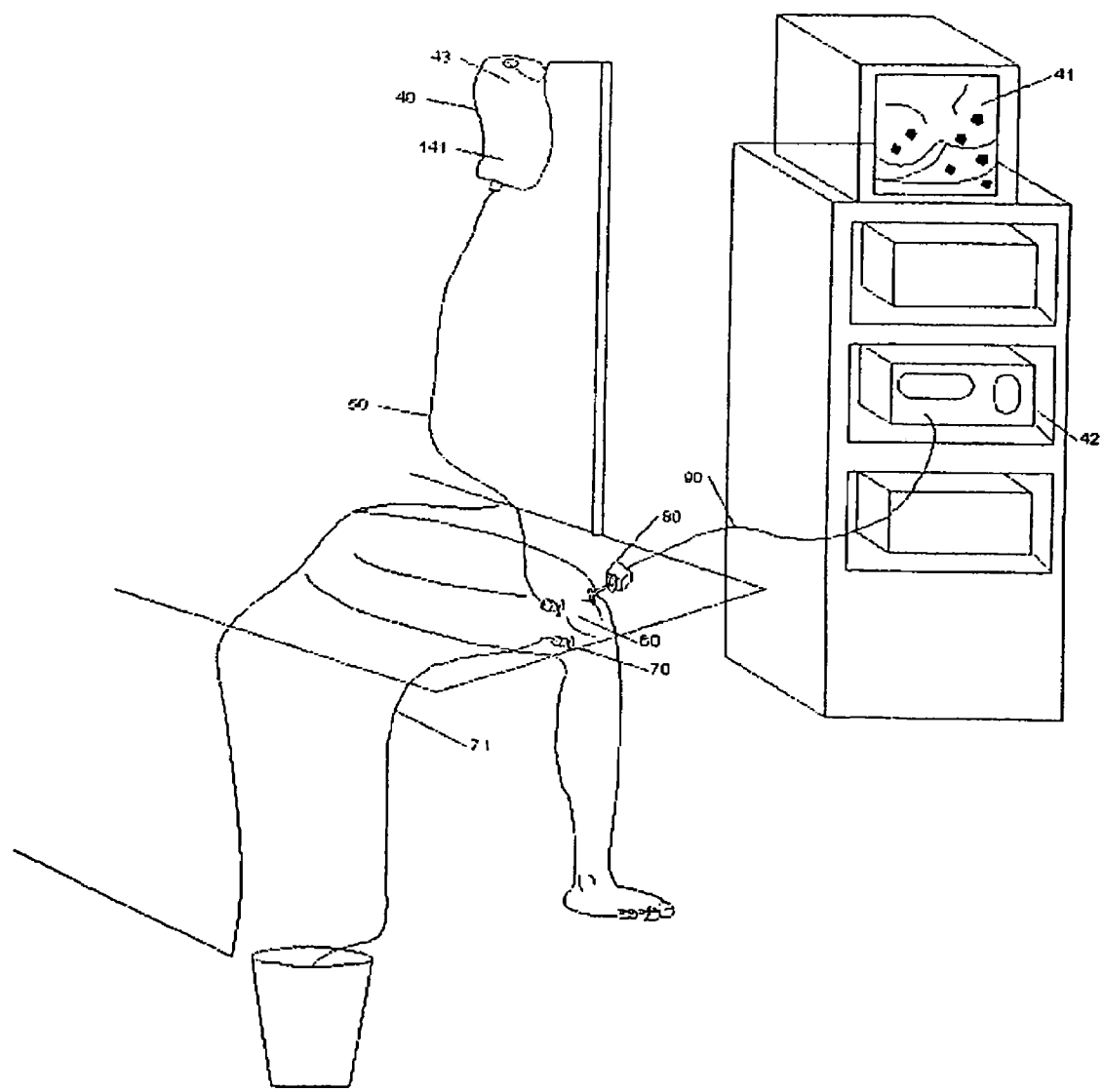
FIG. 1 is a view of an irrigant delivery system.

Best Modes for Carrying Out the Invention

This invention provides irrigants with contents and constituent elements that either enhance surgical tool performance or deliver treatment therapies, or both. In one preferred embodiment, the irrigants are used with electrosurgical devices, and include chemical alternatives to increase the utility of the irrigants for use in electrosurgical procedures. Thus the irrigants contain ingredients that promote bio-compatible chemistry that facilitates tissue reactions with electrosurgical processes. Such irrigants may also contain compounds that foster healing processes or cause the expression of desirable genetic outcomes or augment tissue identification and assessment.

The irrigants of the invention may, in one embodiment, include biologically enhanced agents for temporarily bathing of living tissue with biologically and electromagnetically active elements, designed to function in concert with and in a synergistic manner with specific instrumentation, such as electrosurgery devices. Formulation and application of specifically engineered irrigants to instrument-specific procedures is designed to improve instrument performance, thereby providing a superior result in surgical or other medical applications.

In one embodiment wherein electrosurgery devices are employed, the irrigants and devices are used in endoscopic procedures. Examples of irrigants suitable for endoscopy include light filtering irrigants, utilizing density absorption techniques to block specific wavelengths of light and improve visualization of any portion of the light spectrum; magneto-hydrodynamic irrigants, utilizing magnetically "orientable" molecular structures that allow for area-specific magnetically induced pressures to be created; RF signal transduction enhanced irrigants, for assisting RF-based instrumentation to irradiate specific surgical sites with improved power conduction, thereby lowering net power requirements and output; silicon lubricating irrigants, for assisting silicon-based nano-devices in navigating relatively long distances to surgical sites to perform repair functions; nano device fueling irrigants, for providing a fuel source for nano-devices to perform extended operations within the human body without the need to incorporate fuel cells or have RF energy signal conversion electronics; irrigants for control of gene expression, as either primary or secondary effectors of gene expression, such as use of RF energy to activate inert chemical compounds to change structures to a structure that either promotes binding or activation functions; irrigants that perform tissue nutrition, regeneration or other such processes; irrigants that perform modulation upon indirect biologic systems or functions, such as immune, endocrine, or central nervous system, inflammatory or healing responses; and other engineering irrigants for similar functions that enhance device operations.

In one embodiment, the invention provides an engineered irrigant component that includes a biologically-based composition for temporarily tagging or binding to living tissue. The disclosure and teachings of U.S. patent application Ser. No. 09/952,538, Method Of Performing In Vivo Real Time Tissue Histology In Surgical Procedures, to Augé, is incorporated here by reference. The composition may include a molecular probe with photoactive elements that emit photons from the ultraviolet to infrared spectrums. Alternatively, the composition may include molecular probes of the type that is known as self-fluorescing, a chemiluminescence process, which emits photons in a specified range when in the presence of the appropriate chemicals that drive the luminescence process. Alternatively, the molecular probe may be of the type that is fluorescing, such as a fluorophore, which emit photons in a specified range when impacted with a light source of a known and specific frequency. The composition may be composed of several suitable biologic elements that are targeted to join with highly specific tissue types, depending on the specific intent of the medical indication or procedure for which the molecular probes and compositions are developed. In another embodiment, tissue-specific stains can be used in a similar manner to color tissue utilizing similar means to identify component tissue structures.

As used herein, molecular probe includes any component with photoactive elements that emit, or can be made to emit, photons from the ultraviolet to infrared spectrums, including visible spectrums. The molecular probe thus includes self-fluorescing, chemiluminescent, fluorescing, and phosphorescing reagents, including materials that emit photons in response to excitation by radiation of a particular wavelength, including both short-lived and long-lived excitation states. A molecular probe further includes any component with color elements, such as a stain, that reflects photons at a specified wavelength.

In one embodiment, the engineered irrigant component consisting of a molecular probe includes a functional moiety, which serves to bind the molecular probe to a target of interest, including a region or area of physiological interest, such as a proteoglycan.

In yet another embodiment, the engineered irrigant component consisting of a molecular probe is bound, reversibly or irreversibly, to a targeting agent. A targeting agent binds to a region or area of physiological interest. Such binding of the molecular probe to the targeting agent may be by covalent, ionic, or other means.

In some embodiments, the targeting agent may be a peptide or a protein fragment, including a fragment of an antibody. The targeting agent may be made by any means known in the art, including synthetic means and recombinant engineering means.

One preferred target of interest for a targeting agent included with an engineered irrigant component is a proteoglycan. A proteoglycan includes glycosaminoglycans, also called mucopolysaccharides, including but not limited to hyaluronate, chondroitin sulfate, keratin sulfate, dermatan sulfate and the like, generally forming a part of the extracellular matrix of connective tissue.

The molecular probes and associated components of the engineered irrigants are utilized with optical visualization tools such as endoscopes, light sources, and video cameras to allow the surgeon to see specific tissue structures and better understand that tissue's condition or status. It should become clear to one skilled in the art that such tools allow for better understanding of potential treatment of that tissue. The use of these compositions and stains produces the new and unexpected result of enabling real-time tissue status feedback to the surgeon, thereby enabling rapid accurate assessment of tissue condition.

In can readily be seen that a number of advantages result from such examples. Thus the methods and compositions of this invention may be employed to enable new device technologies for minimally invasive surgery. In another embodiment, the methods and compositions enhance currently available visualization technologies with new spectrum filtering and visualization capabilities. In yet another embodiment, the methods and compositions shorten medical procedure time due to enhanced device performance. In yet another embodiment, the methods and compositions provide improved reliability of device performance due to added performance from irrigants. In yet another embodiment, the methods and compositions provide extended device capabilities due to added performance from irrigants. In yet another embodiment, the methods and compositions provide hydrogen-rich or oxygen-rich chemistries that enhance electrosurgical device performance. In yet another embodiment, the methods and compositions provide a fuel source rich media for self-propelled nano-devices to convert into motive work. In yet another embodiment, the methods and compositions provide a lubricant-rich media for self-propelled nano-devices to allow motion or assembly. In yet another embodiment, the methods and compositions provide for combinations of irrigants through multi-port flow switching devices, thereby allowing facile mixing or sequential administration of various irrigants and irrigant constituent elements.

In one embodiment, the engineered irrigants are employed with nano devices. A specific limitation to current micro-electro-mechanical devices hereafter referred to as nano devices, is their limitations of self-powering motive force. Power sources currently available remain excessively bulky for practical application to nano-devices. Size and weight constraints are further exacerbated by the power life of existing battery technology. Engineered irrigants provide the chemistries that enable respiration type or bio-chemical gas liberation type oxidation-reduction reaction based power conversion. Such power conversion can be accomplished in microtubule reactors transduced to provide work at an output shaft for various types of motive force. The ability to autonomously generate power or work eliminates the need for self-contained power storage devices, thereby reducing further the required volume of nano-devices. Additionally, such self-contained power generating capacity by definition requires a fuel source/reservoir, which is eliminated through the fuel rich environment provided by the irrigant media. Nano-devices previous limitation of distance/time to travel to a surgical site is limited only by the ability to immerse the specific surgical site with a suitable engineered irrigant. A nano-device operating in such an environment can take up the engineered irrigant and through a micro-tubule reactor system liberate a carbon dioxide gas component which expands to a gaseous state which is then utilized to provide work output, such as by means of a piston or cylinder type power conversion system to provide rotational shaft work output.

An alternative form of energy conversion can be accomplished through a heat liberating reaction from protein respiration type oxidation-reduction reactions that may be taken advantage of through use of a cyclic thermal-expansion mechanical device to provide shaft-work output for motive force.

In another embodiment of the present invention irrigants are provided and used for delivering tissue regenerating therapeutic compounds to spur the bodies natural healing response systems during the "closing" portion of a surgical procedure. This is done with biochemical compounds that target the autoimmune response system to deliver necessary hormonal, protein, and enzyme structures to specific tissue sites within the surgical wound. Such irrigants foster not only the collagenous tissue rejoining process, but also revascularization and neuro-stimulation healing.

In yet another embodiment of the present invention irrigants are provided including biocompatible, magnetically-oriented hybrid molecules with gene expression compounds. These joint vector-vehicle-therapy systems are capable of being magnetometrically influenced from external of the body, effectively boosting chemotactic behavior in positive gradient environments or counteracting chemotactic effects in negative gradient environments. This is most advantageous for negative gradients where natural immune response may attempt to attach foreign structures within the body. Such molecules that may have efficacious applications for tissue regeneration within a specific tissue structure, but may be seen as foreign elements elsewhere within the body are now more readily and speedily delivered to the target site—before the body can react to render the compounds useless. Perhaps even more important for compounds that may have detrimental effects if allowed to circulate freely within the body, force can be applied magnetometrically to contain delivery of specific irrigant components or compounds to the target site within the body.

The methods, systems and compositions of this invention thus provide a specialized form of drug targeting, utilized in conjunction with irrigants employed for conventional surgical or medical procedures. Conventional drug targeting technologies are described generally in Torchilin V P, Drug targeting. *Eur. J. Pharm. Sci.* 11S2:S81-91 (2000). The benefits described therein, such as distribution at the site of desired effect, high local concentrations, limitation non-specific toxicities and the like are also provided by the methods, systems and compositions of this invention. However, in the prior art these benefits have not been provided in conjunction with an irrigant system.

To one skilled in the art, combinations of the biochemical compounds discussed above become readily apparent for use within the gastro-intestinal system, urinary tract, thoracic cavity, cranial cavity and spinal column. Additional advantages, objectives, and novel features of the invention are set forth in part in the description that follows. It will become apparent to those skilled in the art upon examination of the following or may be learned by practice the complete application of the technology disclosed herein.

FIG. 1 illustrates a multiple irrigant pump delivery system for use with the irrigants of this invention. Engineered irrigant components 141 are suspended in irrigation solution 43 contained within an irrigant polymer dispensing pouch or container 40. Fluid conduit 50, a tube set or pipe, is used to convey the engineered irrigant components to surgical site 60. Fluid discharge conduit 71, similarly a tube set or pipe, is used to convey the effluent of the surgical site away to disposal by means of outflow portal 70. Surgical video camera 80 is inserted into surgical site 60 for endoscopic surgical site viewing. The image is captured via camera 80 and transmitted via video signal transmission cable 90 to a primary image-processing unit 42. The image is processed into a standard video signal, such as a broadcast compatible image signal like NTSC, PAL, or a digital image, and delivered to display monitor 41.

In the use of the system of FIG. 1 in endoscopic procedures irrigation fluids 43 are applied to the surgical site, such as the joint depicted, to cleanse the surgical site, distend the surgical site, and clear the field of view. Thus FIG. 1 depicts a system employing a typical underwater endoscopic system for performing minimally invasive surgery on the human body. One or more engineered irrigant components 141 are combined with irrigation solution 43. The engineered irrigant components 141 can be injected into pouch 40, preferably by means of a portal provided for such purpose, or may be included in the pouch 40 at the time of manufacturer thereof. Irrigation solution 43 together with engineered irrigant components 141 are delivered through tube 50 to surgical site 60 under either gravity flow or forced conditions, such as by means of a pump, to both irrigate and distend surgical site 60. Engineered irrigant components 141 may include chemotactic components, such that the chemotactic components accumulate at desired tissue locations, or may include magnetically movable components, including components that may be moved by magnetic means through or into environments not otherwise accessible because of any of a variety of physiologic considerations. Irrigation solution 43 thus provides the function of clearing the field of view and maintaining joint capsule distension, and providing a media for delivery of engineered irrigant components 141.

Once in contact with internal tissue structures of the human body, engineered irrigant components 141 combined with irrigation solution 43 are capable of delivering multiple therapeutics simultaneously to the surgical site. For example, it is known that many diseases directly influence the cellular structures of both soft and hard tissues within the human body. By applying tissue specific therapeutic treatment irrigants simultaneous with site-specific surgical procedure outcomes are improved with respect to healing and recovery time. Combination of such irrigants can be accomplished via multiple means, such as pre-manufactured in a sterile environment, injection into a sterile bag prior to use, or combined metering at the time of surgical procedure.

Figure 2:
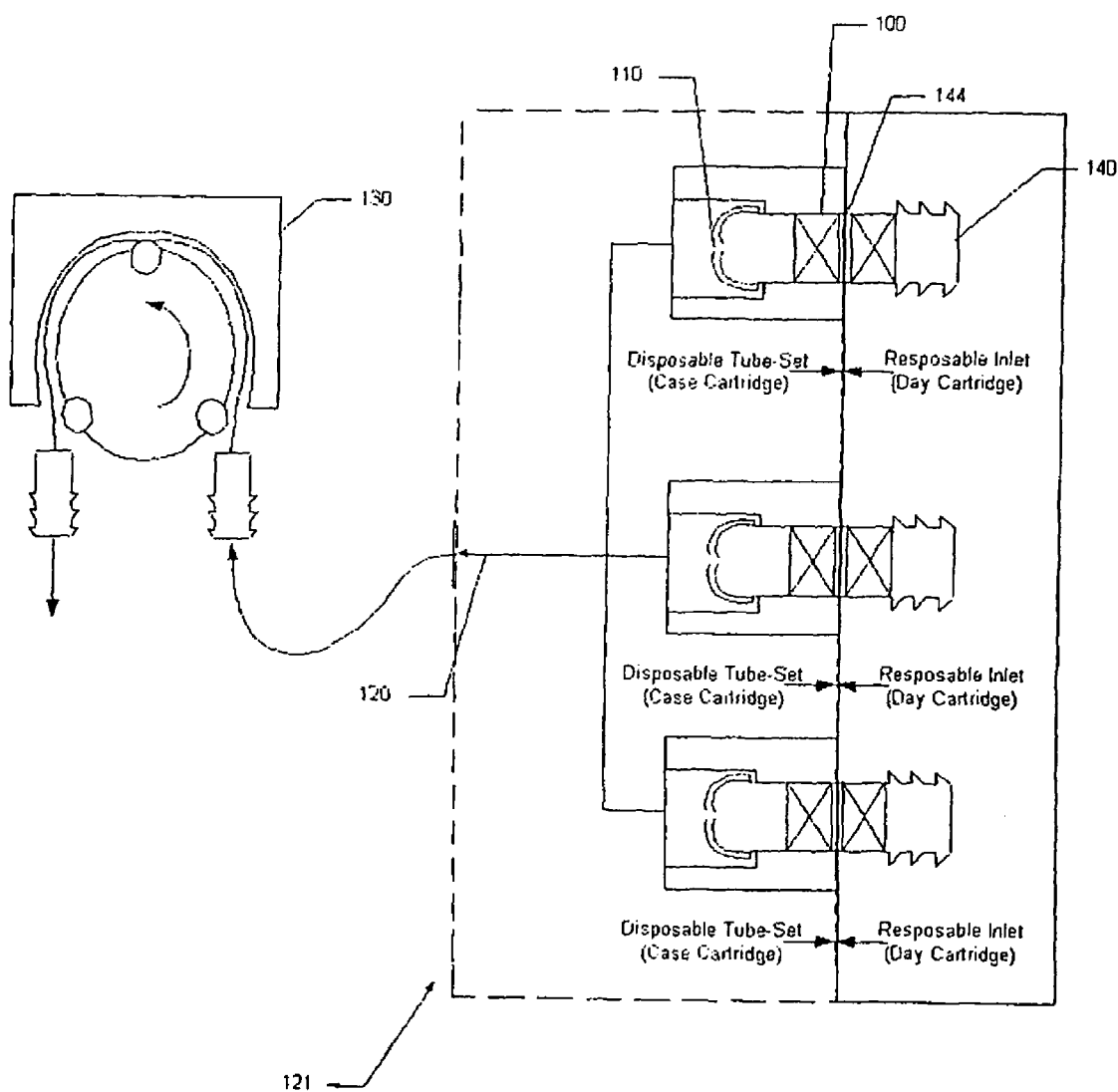
FIG. 2 is a view of a multiple irrigant pump delivery system.

FIG. 2 illustrates an embodiment of a multiple irrigant pump delivery system that may be employed with this invention. Through use of this system, the ratio or quantity of engineered irrigant components 141 may be altered during the surgical procedure. Irrigant metering manifold 121 may be positioned at any point prior to delivery to the surgical site. Engineered irrigant components 141 enter metering manifold 121 at entry nozzle 140 and are directed through boundary seal 144 and thence to and through standard metering needle or ball type valve 100 to microbial seal polymeric diaphragm valve 110. Valve 100 can be a polymeric metering valve, such as a dual needle block valve. Valve 100 can be controlled by manual adjustment, or may be controlled by remote means, such as through use of an electrical control system. Microbial seal 110 may be a check valve, such as that disclosed in U.S. Pat. No. 6,202,901 to Gerber and Deb. Use of manifold assembly 121 permits large volumes of different engineered irrigants components 141, which are frequently costly, to be maintained sterile for use in multiple procedures with different patients. Boundary seal 144 provides a juncture or connection between disposable components, including the valve 100 and microbial seal 110, and components that may be used with multiple patients, including the entry nozzle 140 of the cartridge set, and the bag or other receptacle for engineered irrigant components 141.

To ensure adequate emulsification of all irrigant components, static mixing vane tube 120 is placed in the common disposable manifold section before delivery to pump 130, such as a peristaltic pump, with subsequent delivery to the surgical site. The cartridge sets are conventionally made of a polymeric material. Metered blending of engineered irrigant components may be accomplished through preset valve 100 opening percentages for specified irrigants to produce the desired constituents of the irrigation solution.

In one embodiment, the multiple irrigant pump delivery system of FIG. 2 includes the use of glycine, normal 0.9% saline and lactated Ringer's solution during arthroscopy, with each reservoir in FIG. 2 holding a different irrigant. The system is used during surgery to switch between irrigant solutions depending on the particular treatment encountered. For example, a high-energy monopolar electrocautery wand will only work in glycine, and thus the glycine-based irrigant is employed when that device is used. When a bipolar RF electrosurgical wand is employed, the metering manifold can be switch to normal saline, the preferred environment for such device. Similar changes can be made to the local surgical environment based on the specific and immediate treatment purpose. Thus irrigants with components such as glucosamine, hyulronic acid or the like can be employed for therapeutic effects.

Figure 3:
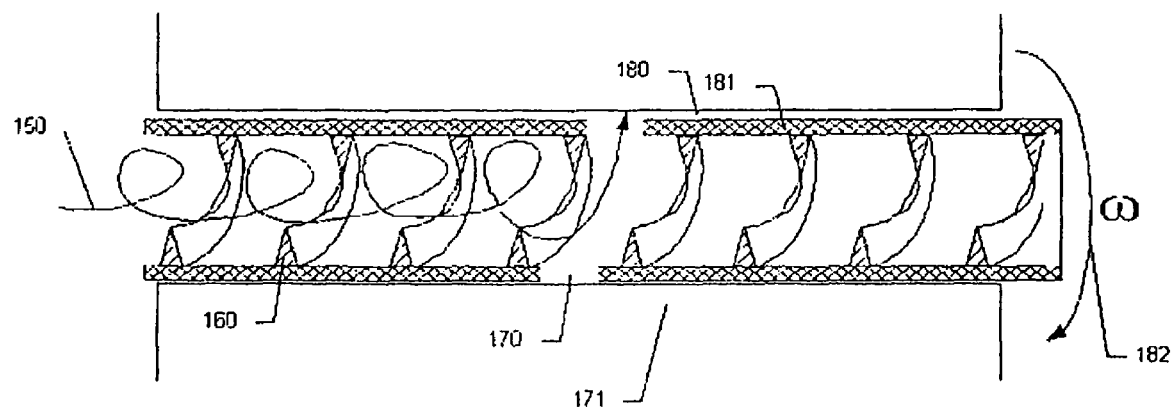
FIG. 3A is a view of a lubricated journal shaft of a nano-device.
FIG. 3B is a view of a nano-tube power conversion system.
Figure 3:
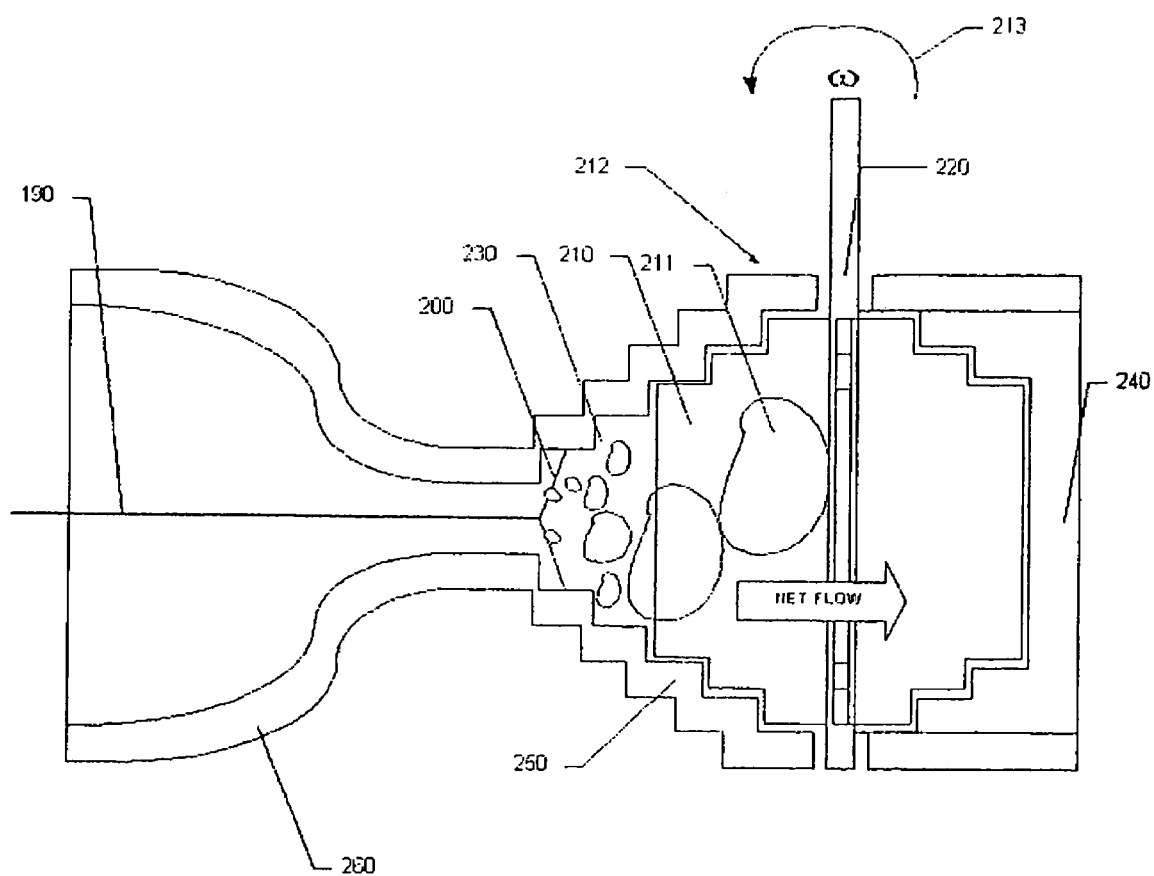

As shown in FIG. 3A, engineered irrigant components 141 can be utilized for purposes beyond tissue-related therapeutics, such as acting as a lubricating agent for nano-devices within the human joint capsule or any operating space that can be created by either surgical process or the nano-device itself. In order for such devices to perform auto-motion some form of work must be translated into a driving force. This can be in the form of pressure-volume work, heat transfer, shaft work or some combination of the above. In FIG. 3A shaft 181 is shown that produces rotational mechanical output 182 to power a drive mechanism such as a propeller, gear, wheel, track, turbine, or other suitable drive device. Integral to such a nano-device shaft is an auto-rotating irrigant entrainment system designed to "draw" irrigant lubricant 150 into the central portion of shaft 181 and down to lubricating exit portal 170. Rotation in shaft 181 creates a positive displacement vane "pumping" effect along the internal walls of shaft 181, in part through the action of internal induction vane 160, and centrifugally draws irrigant lubricant 150 down the central axis of shaft 181. Static wall pressure at lubrication exit portal 170 forces the fluid out of the central shaft annulus and into annular space 180 between shaft 181 and support bearing surface 171, thereby creating a journal bearing-type fluid lubrication process. Irrigant lubricant 150 may be understood to be a type of engineered irrigant component 141, and may in this instance include a gelatin enhanced isotonic solution, glycerin enhanced neutral buffered solution, or other compositions known to those skilled in the art which serve as a lubricant.

FIG. 3B depicts a reaction wick gas expansion paddle wheel drive system for use with latent carbon dioxide gas enhanced irrigant solutions. This drive system may be employed with any of a variety of nano-devices. Engineered irrigant component 141 includes latent carbon dioxide gas components that are easily liberated via an acetic acid reaction. Hydrophilic wick 190 is used to entrain the specific irrigant chemical composition much like a kerosene lamp wick does fuel. Thus hydrophilic wick 190 creates an adsorptive gradient along which the irrigant is drawn. Hydrophilic wick 190 is contained within a fluid capture converging nozzle 260. Engineered irrigant components 141 traverse the length of wick 190 to reach reaction lattice 200, which is composed of an acetic acid or similarly enriched porous silicon, and chemically reacts with engineered irrigant component 141 to release latent carbon dioxide as a gas. Reaction lattice 200 is contained within gas expansion plenum chamber 230. As carbon dioxide is released, carbon dioxide bubbles accumulate, resulting in formation of a surface tension "pressure". Further liberation leads to coalescence of discrete bubbles 211, and net bubble movement outward from plenum chamber 230. Still further carbon dioxide liberation results in net flow forcing past paddle wheel paddles 210. Paddle wheel chamber walls 250 are machined or etched in a stair step pattern to act as a bubble flow check valve to prevent enlarging bubbles from "back-flowing" out the wick section. Optionally reaction plenum chamber walls 250 enhance carbon dioxide liberation through acetic acid "doping" of silicon wall sections to provide further reaction chemistry to boost overall reaction rates. Similarly, nozzle walls 260 may optionally enhance irrigant entrainment through doping with hydrophilic desiccants such as alumina powder or various salts, as are known to those skilled in the art. Continuing liberation and net gas flow is exhausted via paddle wheel exhaust tube 240. Movement of the bubbles forcing each paddle to move creates shaft work output 213 by means of rotation of output power shaft 220, which work output 213 can be utilized for auto-motive drive systems. As the continuing gas reaction process proceeds carbon dioxide gas is forced out of the exhaust tube 240, and may be partially reabsorbed by the irrigant or metabolized by normal body metabolic functions.

Figure 4:
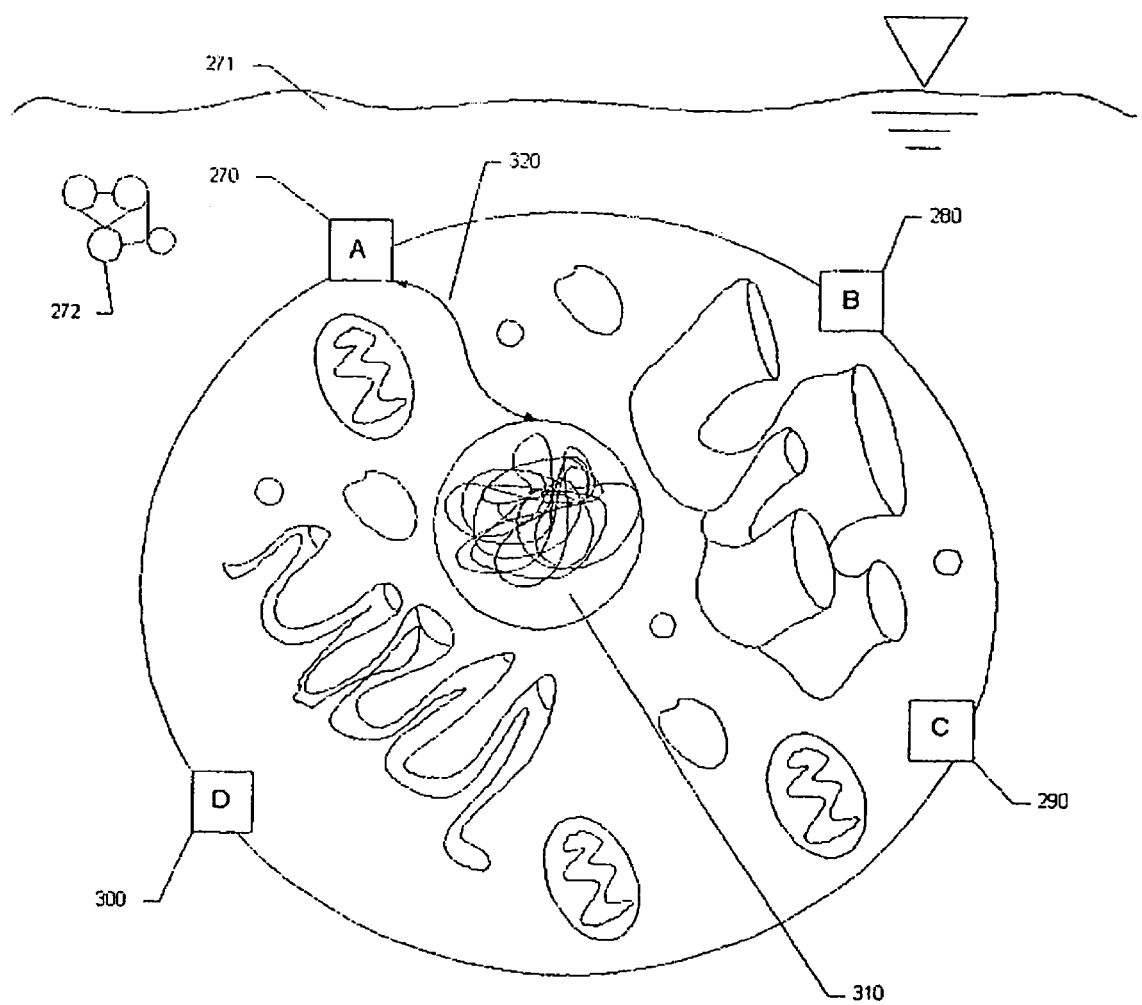
FIG. 4 is a view of a general cellular representation and surface membrane and receptor sites.

In FIG. 4 a human cell is depicted, with different target receptor sites for irrigants graphically represented. The target sites may be employed to enhance tissue growth response, inflammatory response, and various potential membrane transport mechanisms. Thus FIG. 4 illustrates cellular level irrigant activity. A typical human cell is immersed in irrigant immersion solution 271, which solution 271 contains multiple cellular receptor activator components 272. In one embodiment, component 272 attaches to cell receptor 270, which component 272 carries transcription agents for mRNA 320 insertion and delivery to cell nucleus material 310 for the specific purpose of triggering cellular response at the genetic level. Intra-surgical use of engineered irrigants thus enables access to cellular structures and cytoskeletal triggers that are linked to gene expression. Site 280 is an ion channel site that is activated by ATP, Na+, or K+, and may be employed to trigger cellular excretions, such as hyaluronic acid. The resulting hyaluronic acid in turn is used by the extra-cellular matrix of cartilage to form proteoglycans thereby improving joint lubricity, load bearing capability, and mobility. Control of such interactions at the cell membrane can induce certain cell types, particularly inflammatory cells, to phagocytosis. Such processes are useful in nearly all procedures that involve tissue resection and removal. Irrigants that are enhanced with components that are capable of transcription can engage cellular receptor site 270, and provide means for mRNA transcription 320. Engaging transfer RNA can be used to control genetic cellular response to induce mitosis, lysis or other relevant applicable cellular activity that can stimulate tissue structural repair and rejuvenation. Alternatively cytoskeletal location 290 can experience mechano-transduction that alters cytoskeletal structure, which in turn induces changes in gene expression. Cell receptor site 300 represents a viral, bacterial, or prion transvection channel that can induce changes in gene expression. The irrigant immersion solution 271 may further include any of a variety of emulsifier or nutrient components, such as a surfactant protein or acetate-based binder, that allows for hydrophobic molecules to be used in a wetted environment.

Figure 5:
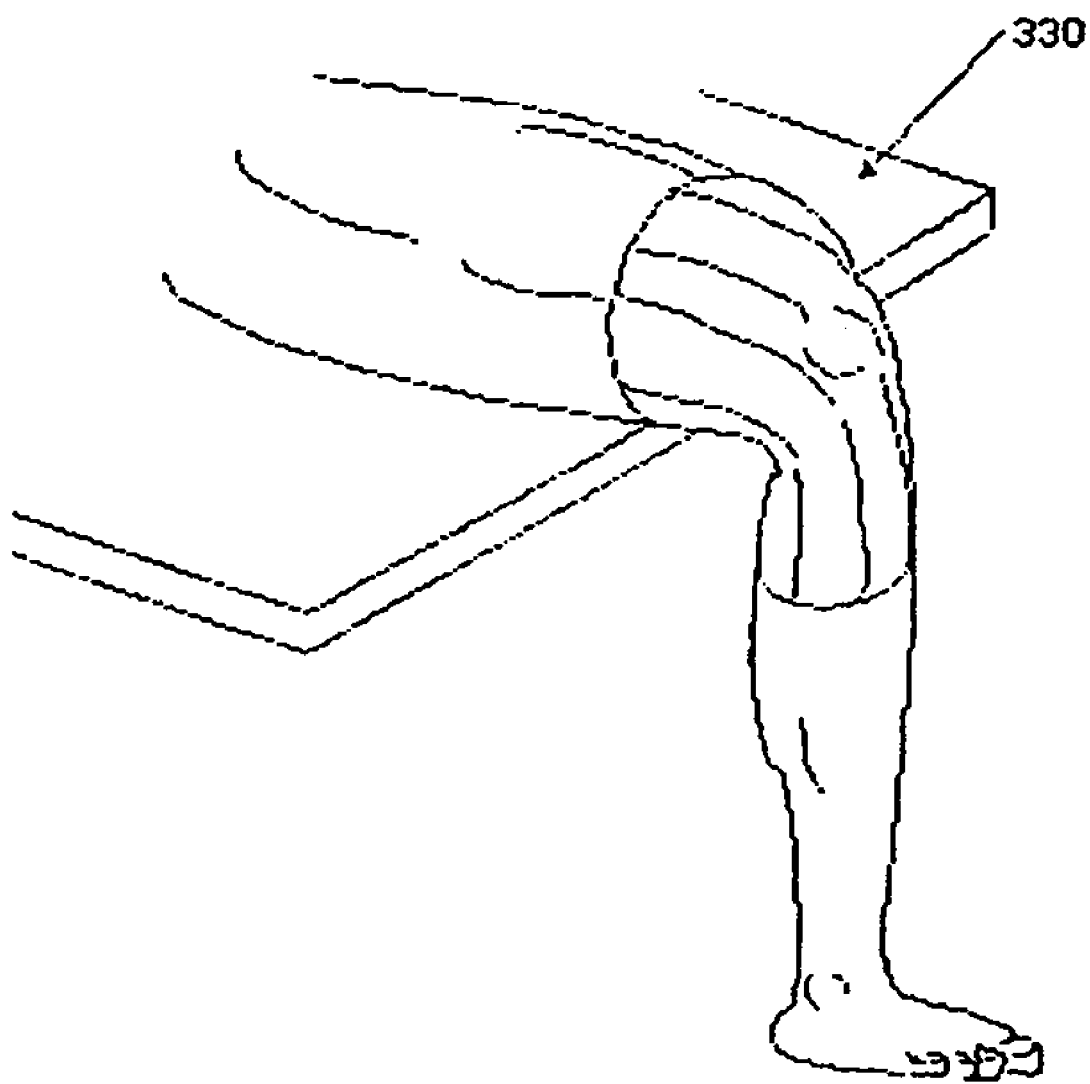
FIG. 5A is a view of a transdermal brace or patch for infusing irrigants.
FIG. 5B is a cross-section view of a transdermal patch.
Figure 5:
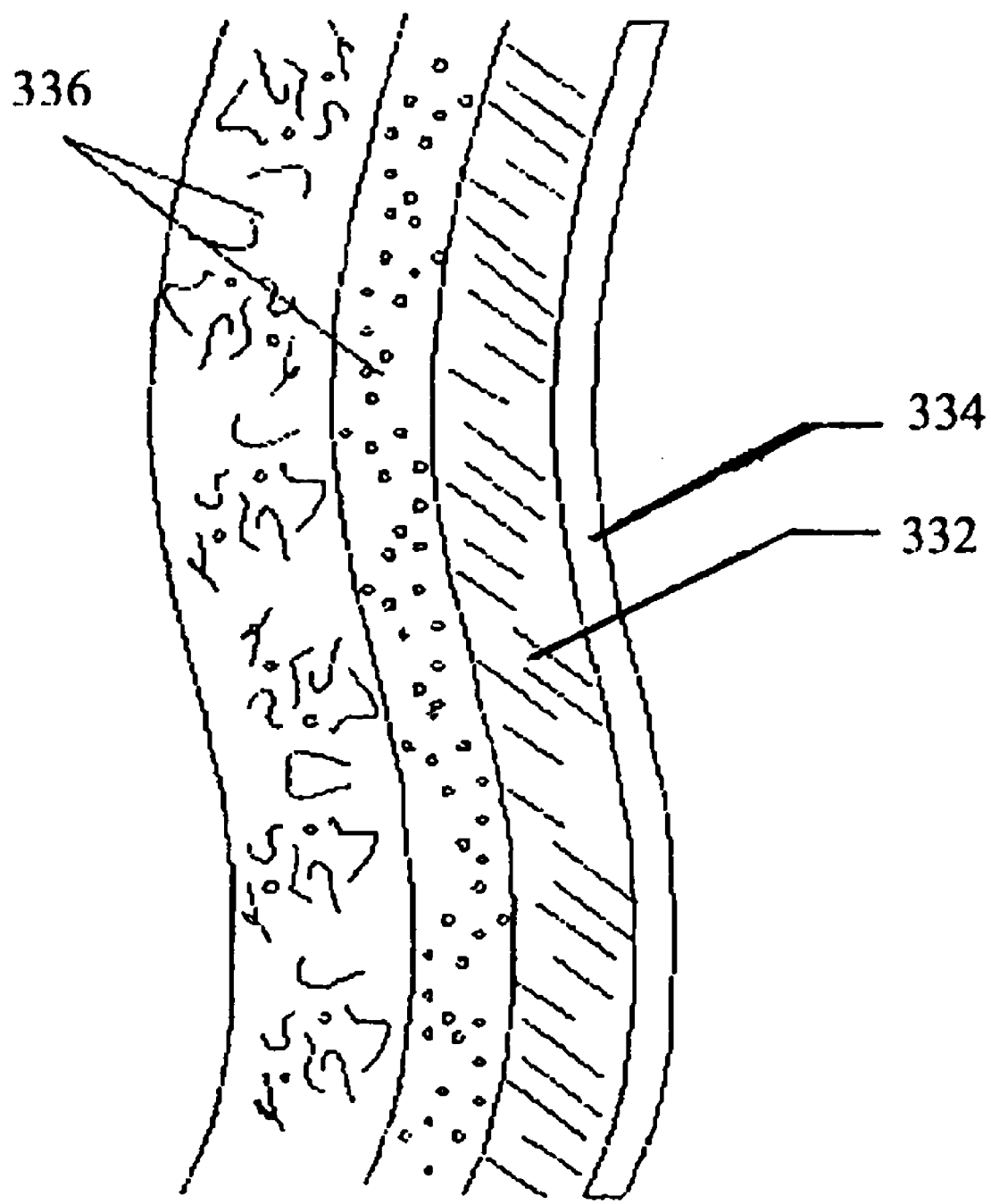

In FIG. 5 A transdermal patch 330 is shown as a component of an elastic knee brace, such as those made of a soft woven material. In FIG. 5 B the cross-section of transdermal patch 330 is shown. Woven elastic material 332 is formed into the shape of a typical knee brace and gel encapsulant backing 334 is adhesively bonded to material 332. The backing 334 may be an acetate film or other similar film. One or more engineered irrigant components are suspended in gel compound 336 and held in close dermal contact by the elastic form-fitting material. In this method of use trans-dermal migration of irrigant components is possible, including mechanisms employing chemotactic attraction. These methods may be employed as a pre-treatment modality, with application 24 to 48 hours prior to surgical procedure commencement.

Figure 6:
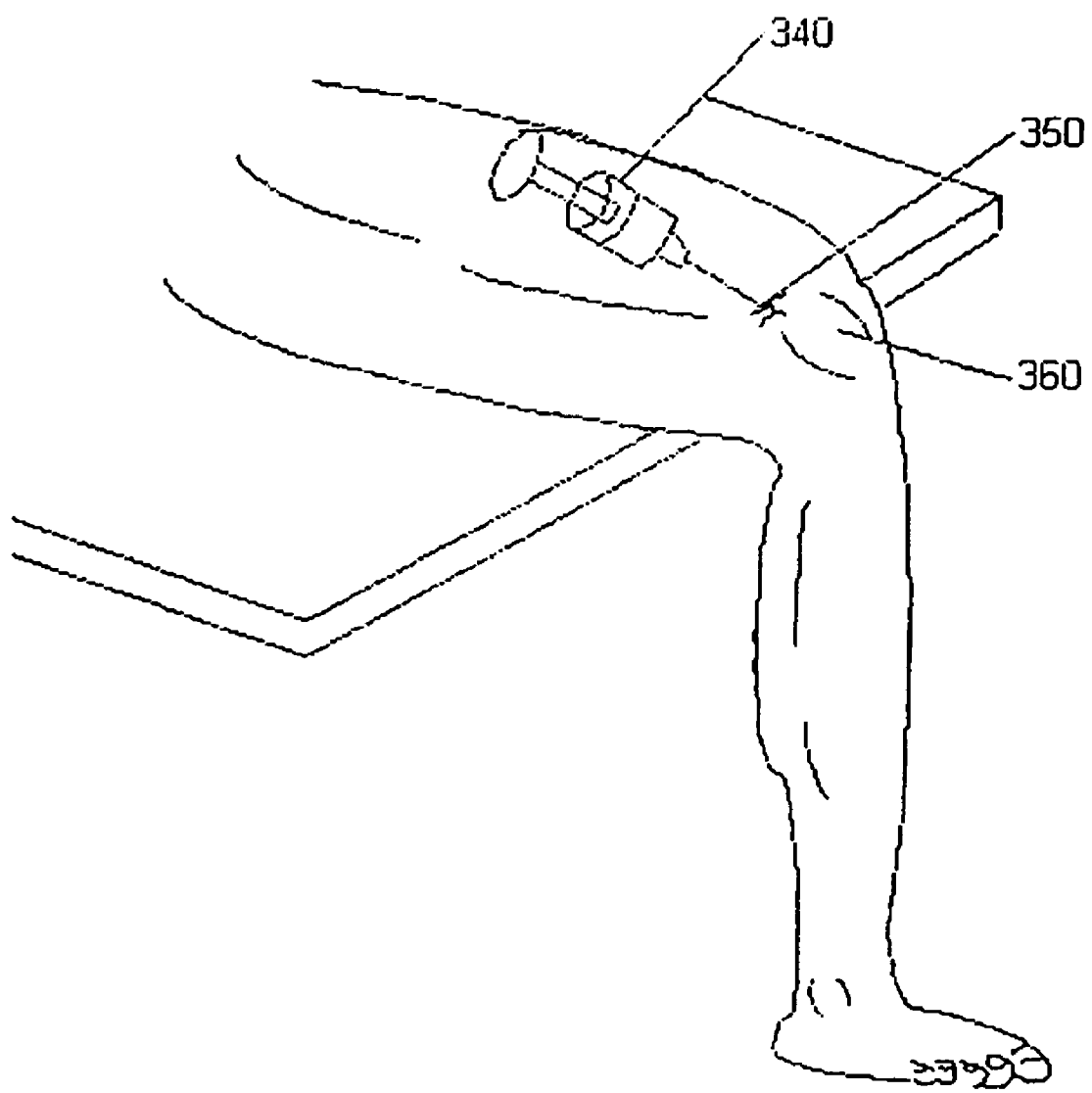
FIG. 6 is a view of a typical injection of such an irrigant.

As illustrated in FIG. 6 engineered irrigant components can also be delivered through use of a standard surgical syringe 340. The engineered irrigant components can be delivered prior to surgery, such as about two to four hours prior to surgery, or can be delivered in the initial stages of a surgical procedure. Epidermal puncture 350 is made to enter joint space 360 and thereby deliver the engineered irrigant components in a normal manner using the syringe.

Figure 7:
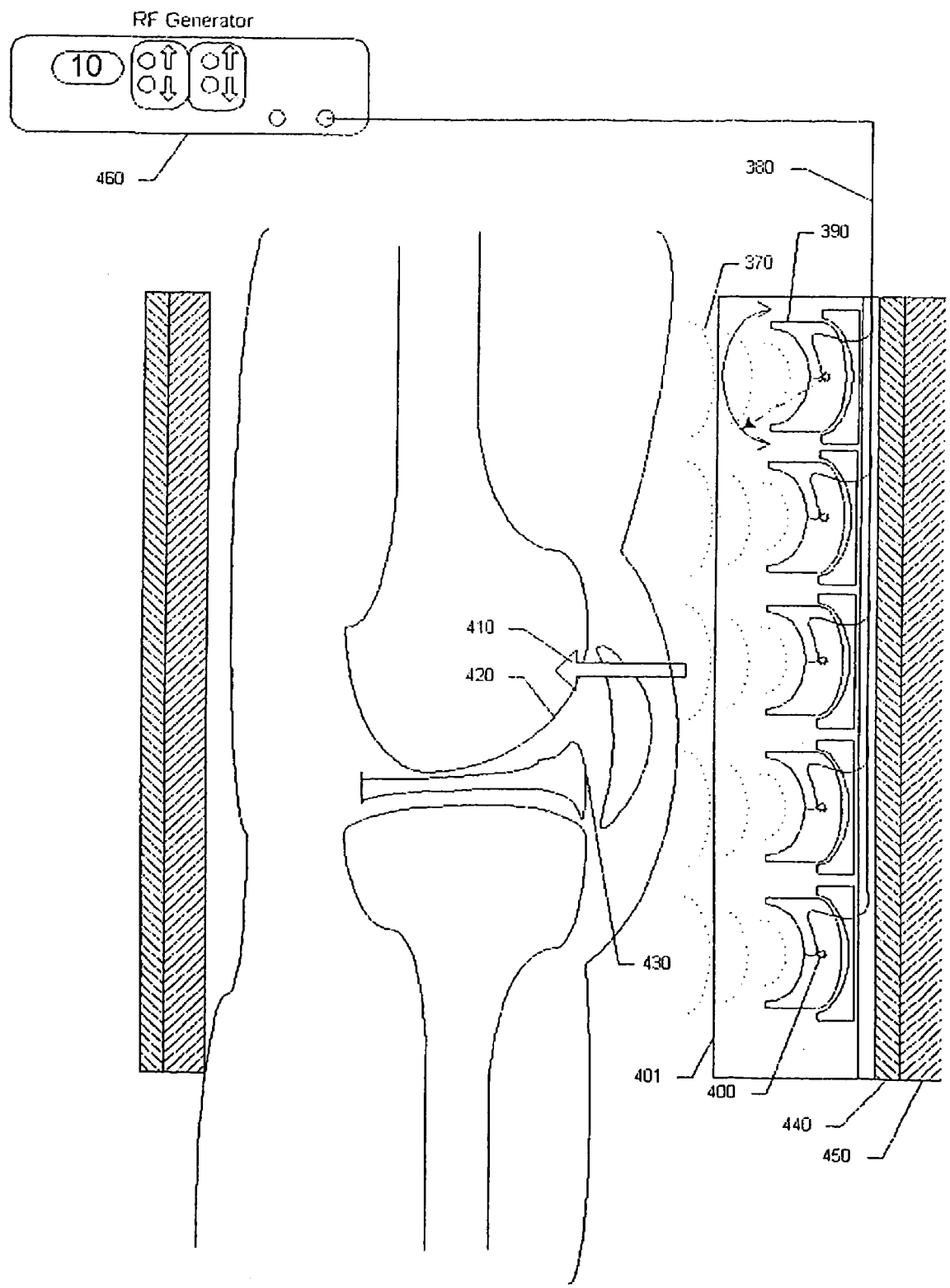
FIG. 7A is a view of a magnetometric force inducer for applying artificial pressure to irrigants for delivery into entire tissue structures.
FIG. 7B is a view of the magnetic field acting upon the irrigant that is magnetically orientable.
Figure 7:
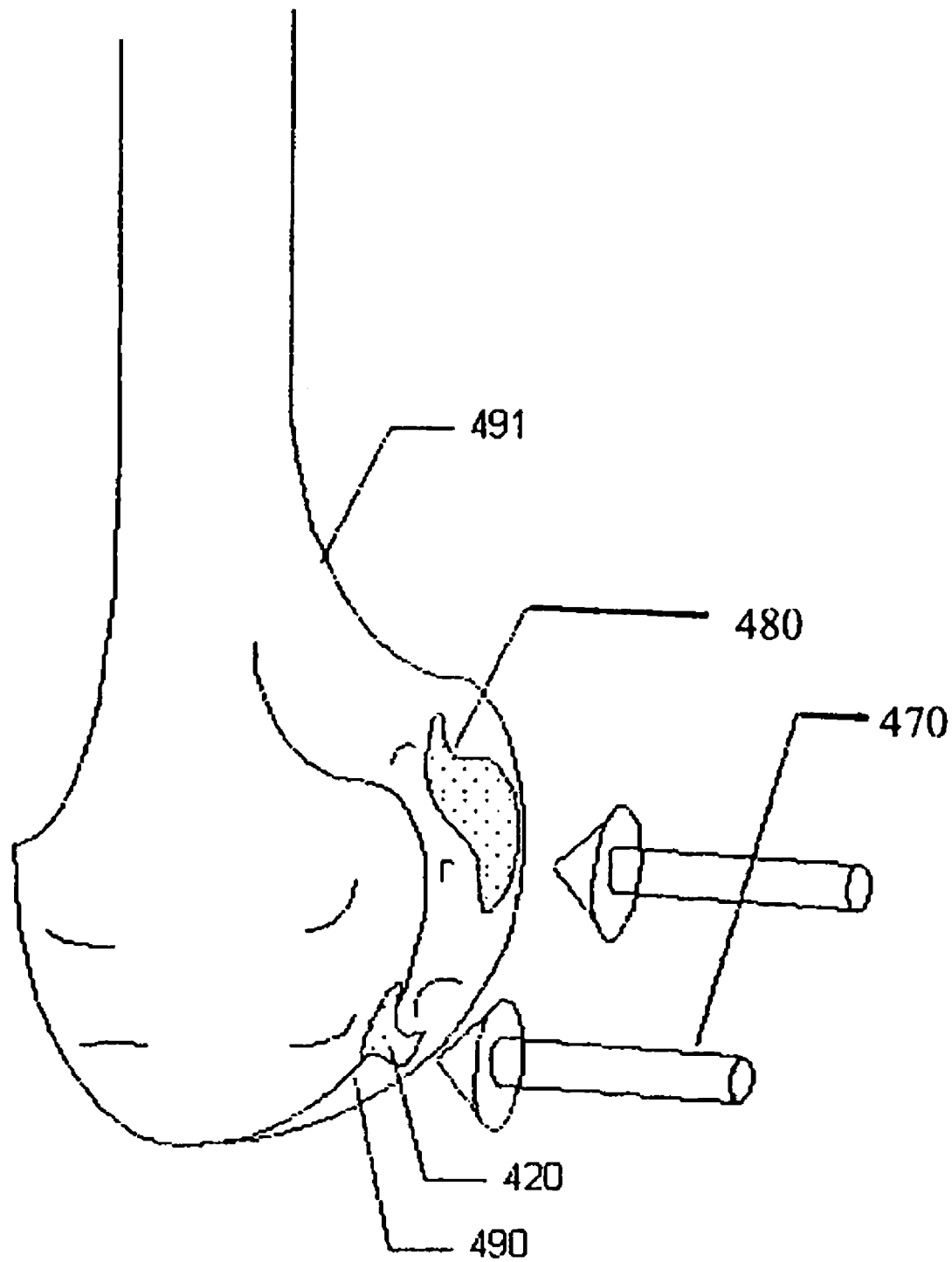

FIG. 7 A depicts an apparatus for applying magnetometric force to magnetically orientable molecules contained as an engineered irrigant component. Variably positionable reflector antennae 390 are used to broadcast electromagnetic waves 370 in a directed and concerted manner. Arrays of reflector antennae 390 are formed and positioned so as to create an electro-magnetic (EM) field potential gradient 410. The EM field gradient delivers a repulsive force to all elements within the EM field of influence. Molecules whose net electric potential are "susceptible" to the tuned frequency of emissions from the reflector antennae array are pushed in the direction of EM field gradient 410. The net rate and force with which these molecules can be pushed is proportional to the power output of the reflector antennae 390, which in turn is governed by the power delivered from the high frequency generator 460. High frequency alternating current is applied to primary conductor 380 and delivers power to the reflector antennae array and creates the net EM field. Each reflector antennae 390 is positionable and/or rotatable over a range, such as over a range of ninety degrees, and is held in place by positioning means 400, such as a ratcheting pinion assembly. The EM field reflector antennae array assembly 401 is enclosed in a flexible membrane container such as a semi-rigid neoprene or similar polymeric material. The assembly may be "potted" to bond the array to the backing wall of the flexible enclosure. The array assembly is optionally bonded to EM shielding layer 440, containing metal foil or other suitable EM deflecting materials. In one embodiment, the device can be bonded to flexible backing material 450. Flexible backing material can form a part of holding means for securing assembly 401 in a fixed position relative to a determined portion of the patient's anatomy.

The assembly 401, together with RF generator 460 and other components can be employed post-operatively, to target tissues sites within the body. An engineered irrigant component including magnetically orientable molecules with a net electron charge repulsed by the EM field, including the net Poynting EM vector 410, is instilled at the surgical site, either during surgery or subsequent thereto. In the example depicted in FIG. 7 A, human chondyle 420 and meniscus 430 are targeted by EM vector 410 to produce a net EM gradient of energy or potential, with EM waves 370 are tuned to the molecular natural frequency of the engineered irrigant component. By use of the device as shown in FIG. 7 A, a force is created via the EM field such that the engineered irrigant component is directed by the net vector force of EM vector 410 toward the target site regardless of osmotic or other chemotactic forces at work naturally. Site specific agents may be complexed or otherwise bound to the engineered irrigant component, effecting site specific delivery of a therapeutic agent, such as to chondyle 420 or meniscus 430. The ability to direct the engineered irrigant component results, in part, from positioning means 400, such as a pin-ratcheting assembly that allow for graduated rotation and holding of each antenna 390 in the array. Each antenna 390 in the array is optionally positioned within a semi-flexible membrane that provides protection to the epidermis from direct contact with array 401 and helps to maintain the relative position of array 401 with respect to the target site within the body. The membrane also optionally functions as an enclosure for array 401 to provide protection from environmental factors such as moisture, heat, impact, and the like. The high frequency electrical signal for each antenna 390 can be delivered as a single combined waveform for all reflector antennae 390 in array 401, or can be delivered via individual oscillating circuitry as independent signals to each reflector antenna 390 in array 401. The type of signal and its specific frequency are set within the range of preferably 100 kHz and 100 GHz, for applications utilizing engineered irrigant components as disclosed herein the frequency is more preferably within 400 kHz and 100 GHz. The energy signal is created using high frequency generator 460 and delivered via high frequency insulated cable 380 to the antenna array 401.

FIG. 7 B depicts surgical sites 420 and 480 on the surface of human femur 491, and specifically femoral chondyle 490 with a chondylar cartilaginous surface. Molecularly magnetically orientable engineered irrigant is shown adhering to surgical sites 420 and 480 of the cartilaginous tissue structure. EM field Poynting vector 470 is shown, which directs magnetically orientable engineered irrigant molecules against the chondyle 490. Using this approach engineered irrigant components that are normally cleared from or absent from the tissue structures, by chemotactic or other means, can be physically position adjacent the tissue structures for the express purpose of delivering therapeutics. Utilizing the device of FIG. 7 A therapeutic agents can be contained by positioning the antennae array 401 in such a manner as to create an EM field that contains and maintains therapeutic concentrations at beneficial levels and delays osmotic diffusion and dispersion of the therapeutic agents. Because normal diffusion, metabolic transport, chemotactic, and osmotic forces can be overcome dynamically, the dosage requirements and therapeutic concentrations can be lowered, thereby diminishing deleterious side effects of conventional drug treatments.

Magnetically orientable molecules or magnetically orientable engineered irrigants include solutions with ferrofluids, including ferrous components, which may be magnetically targeted. It is known, for example, that magnetic fields can be employed to control flow, as is disclosed in Grant K M, Hemmert J W and White H S, Magnetic field-controlled microfluidic transport, *J. Am. Chem Soc.* 23:124 (2002). Similarly, magnetic target of drugs, such as to tumors, has been explored. Babincova M, Babinec P, Bergemann C, High-gradient magnetic capture of ferrofluids: implications for drug targeting and tumor embolization. *Z. Naturforsch* 56:909-911 (2001).

It is also known that magnetic fields, such as those employed in magnetic resonance imaging, have effects on immune system and cellular components, such as adhesion of polymorphonuclear neutrophils. Minczykowski A et al., Effects of magnetic resonance imaging on polymorphonuclear neutrophil adhesion. *Med. Sci. Monit.* 7:482-488 (2001). Engineered irrigant components can be employed that have a desired effect on exposure to a magnetic field, such as increased adhesion and the like.

Figure 8:
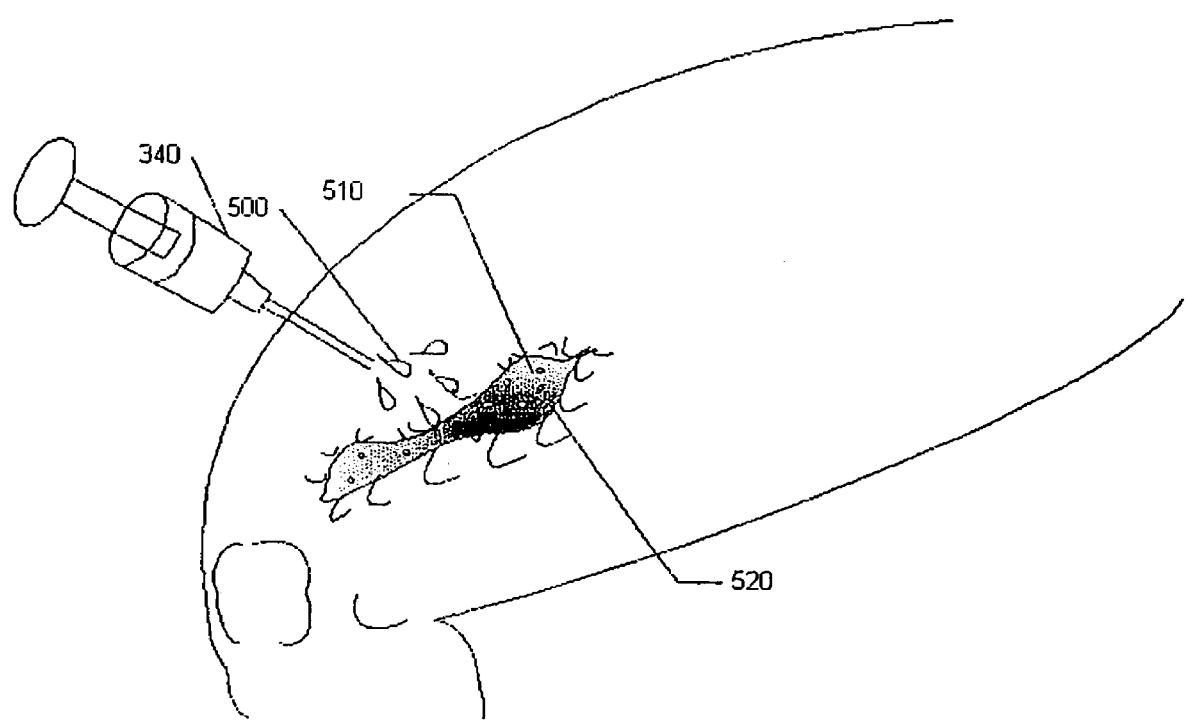
FIG. 8 is a view of irrigation of an "open" wound with an irrigant for applying tissue regenerating or other components.

FIG. 8 depicts irrigant 500 that includes adhesive fibrin components and additional components that accelerate or promote the healing process of sub-dermal collagen tissue structures 510. Factors that can be added include, among others, platelet derived growth factors such as TGFβ-1 factors, insulin-like growth factor, tumor angiogenesis factor, chemotactic factors that causes chemotaxis or other intra- or inter-cellular communication. In general, any collagen soft tissue growth factor may be employed. Such irrigants can be applied to surgical or trauma wound 520 post-surgery as part of a closure procedure to enhance recovery and healing time. Utilizing syringe 340 topical application of irrigants is effected to the site of surgical or trauma wound 520. Irrigant 500 is dispensed into open wound 520 via syringe 340, or may be alternatively be delivered by a lavage irrigating tube set or other appropriate sterile delivery means. Irrigant 500 can thus perform multiple simultaneous operations upon contact with the soft tissue structures, including wetting vascularized tissue and preventing cellular necrosis due to desiccation, delivering irrigant components that modulate soft tissue inflammatory response, delivering other irrigant components that modulate tissue healing and growth response, and delivering other irrigant components such as fibrin that aid in tissue surface 510 adhesion.

Figure 9:
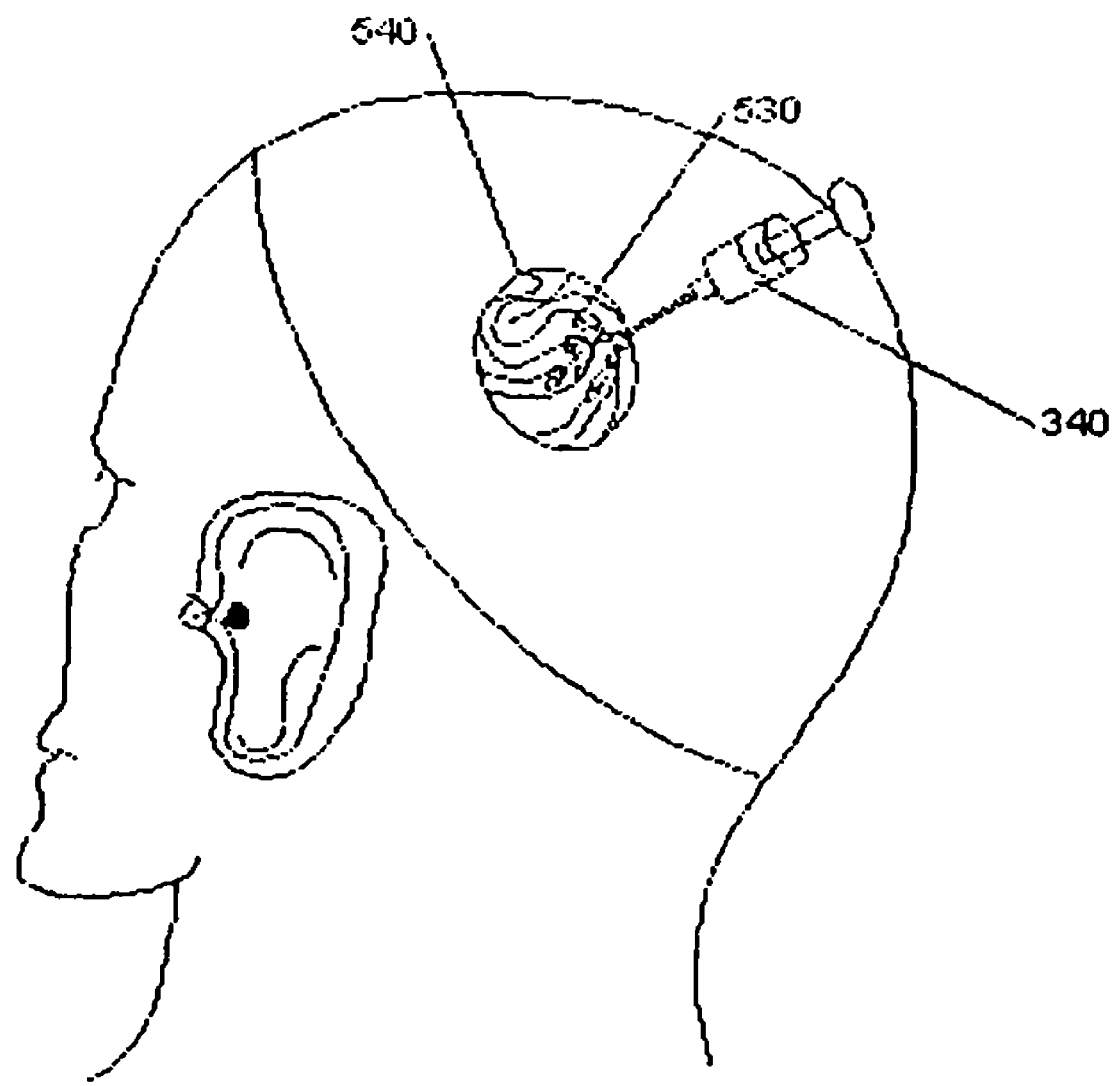
FIG. 9 is a view of the cerebral cavity being irrigated with neural regenerating tissue components.

In FIG. 9 an embodiment is depicted wherein neurological therapeutic irrigant 530, which irrigant 530 includes stem cell-derived amino acids targeted to activate the mRNA of neural cells and promote cellular recovery. Trans-cranial bore 540 is shown for direct site application of irrigant 530 directly to exterior brain tissue by means of syringe 340, or may be alternatively be delivered by a lavage irrigating tube set or other appropriate sterile delivery means.

Figure 10:
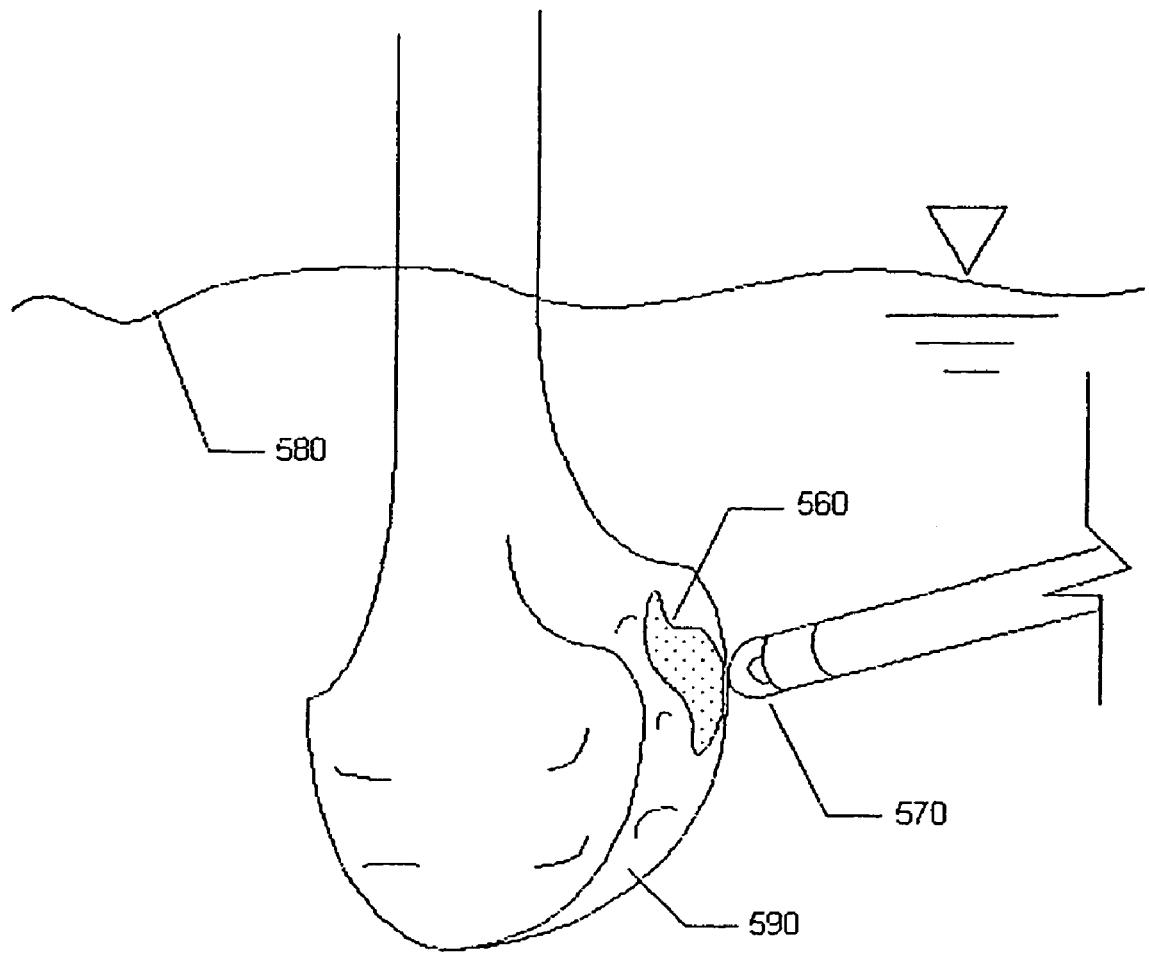
FIG. 10 is a view of use of heat sensing irrigants.

In FIG. 10 an alternative embodiment is depicted, wherein heat sensing irrigants are employed. Engineered irrigant 580 is used for discrete detection of tissue temperature differences. Probe 570, such as an electrosurgical probe used in electrosurgical procedures, is used to impart energy to tissue surgical site 560 forming a part of femoral chondyle surface 590. As the energy is absorbed, the temperature of the tissue rises. It is known that most animal cells cannot survive temperatures in excess of 75° C. and that necrosis occurs in cells exposed to temperatures above this. The maximum temperature range that can be acceptably tolerated by nuclear cells for even brief times is in the range of 65° C. to 70° C.; temperatures in this range for extended periods, or higher temperatures, result in pyknosis or karryorhexis. By using engineered irrigant 580 that includes a thermally activated dye or thermally activated fluorescing compound, the surgeon is able to easily visualize when tissues contacted with probe 570 reaches a safe limit, such as 65° C., and can cease application of further energy. The thermally activated dye or thermally activated fluorescing compound can show temperature differences by means of color or consistency changes over a range. In one embodiment engineered irrigant 580 is visibly a yellow color or fluorescence indicating that a first range of temperature, such as 60° C., has been reached, which color changes to a red color or fluorescence indicating that a second range of temperature, such as 65° C., has been reached. Use of such irrigants assist the surgeon in properly applying the energy released from probe 570 to the tissue structure in question while maintaining temperatures below those that cause irreparable damage to the tissue at the cellular level.

The engineered irrigant 580 may include thermally activated dyes, fluorescing compounds, gelatins and the like, including hydrogels that penetrate cell membrane structures and effectively "read" a temperature change above ambient human body temperature or some other determined temperature. Thus Europium chelates, such as Eu (III) thenoyltrifluoro-acetonate may be employed, which provide a temperature-dependent phosphorescence intensity. Zohar O et al., Thermal imaging of receptor-activated head production in single cells. *Biophys. J.* 74:82-89 (1998); Brennetot R, Georges J, Investigation of chelate formation, intramolecular energy transfer and luminescence efficiency and lifetimes in the Eu-thenoyltrifluoroacetone-triotylphosphine oxide-Triton X-100 system using absorbance, fluorescence and photothermal measurements. *Spectrochim Acta A Mol. Biomol. Spectrosc.* 56:703-715 (2000).

Probe 570 may be an electromagnetic, mechanical, thermal, or chemical energy emitting device capable of delivering surgically or medically useful energy to surgical site 560. In one embodiment, probe 570 is an electrosurgical device employing an RF energy source, for use in tissue cutting, ablation or coagulation.

The engineered irrigants of this invention can be employed with electrosurgical devices, including specifically the electrosurgery devices and methods disclosed in U.S. patent application Ser. No. 10/119,671, entitled Methods and Devices for Electrosurgery, to Morgan, Augé and Prakash, incorporated herein by reference. This application discloses electrosurgery devices that, in one embodiment, employ electrolysis to produce elemental oxygen and hydrogen, with oxy-hydro combustion to effect nerve ablation, tissue ablation, tissue cutting, tissue coagulation, tissue modification, induction of host healing response or other therapeutic responses or modifications. In certain disclosed embodiments the devices in patent application Ser. No. 10/119,671 operate in an aqueous media. The aqueous media can be an engineered irrigant thus is optimized for the specific device employed, such as containing buffers and constituent elements facilitating electrolysis, including salt ions. The engineered irrigant can thus include a salt ion such as an ionic form of sodium chloride, calcium chloride, magnesium bromide, magnesium iodide, potassium iodide, potassium chloride, lithium bromide or lithium chloride. It is further disclosed in patent application Ser. No. 10/119,671 that electrosurgical devices, including those disclosed therein, can cause damage to tissue by means of a deleterious acid-base shift in proximity to the probe tip and adjacent living tissues. The engineered irrigants of this invention can thus further include buffers and the like to minimize the deleterious effect of the acid-base shift.

The engineered irrigant components of this invention thus include glucosamine, chondroitin, hyaluronic acid, steroid hormones, insulin-like growth factors, transcription factors for mRNA, and the like, in addition to the components discussed above. Each of the foregoing is contemplated and included within the meaning of engineered irrigant components. The engineered irrigant components can further include components such as electrolyzed acid water, including such components introduced in situ by means of an electrosurgical device that employs an electrolysis mechanism.

The chemotactic responsive components of this invention includes cells and the like which respond in a classical chemotaxis manner, as well as compositions and compounds, which need not be cells, that migrate or move in response to chemical gradients or chemical stimulants. This thus includes an engineered irrigant component that is responsive to either positive gradient environments or negative gradient environments.

From the description above, a number of advantages to the use engineered irrigants becomes evident. In one embodiment, it is possible to effect delivery of therapeutic biochemical compounds to surgical sites at the time of need. In another embodiment, it is possible to effect accurate and controlled delivery of regenerative and gene expression therapies for tissue structures utilizing magnetometric force applications. In yet another embodiment, it is possible to extend the range of nano-devices, such as for delivery of therapeutic drugs to target sites. Accordingly, the use of engineered irrigants in vivo during surgery provides advantages to the surgeon and patient in improving intervention options, treatment vectors and patient outcomes over prior processes for performing endoscopic surgery. Use of engineered irrigants significantly alters the surgical process by allowing the introduction of new therapeutic elements in the use of engineered irrigants.

Engineered irrigants may be delivered via multiple means, which include but are not limited to injection into the joint prior to irrigation, aliquot injection into a sterile irrigant solution bag for delivery via tube-set or other irrigant delivery means, conventional irrigant solutions formulated with an engineered irrigant in a sterile irrigant solution bag for delivery via tube set or other irrigant delivery means, topical application, such as a paste, via an incision portal, or use of transdermal patch osmosis as an adjunct to a surgical procedure.

Thus it is possible and contemplated, by means of providing immediate site delivery of immune response, inflammatory response, endocrine response or neurological response system receptor activators, to shorten the overall physiologic response time to begin the healing process. It is also possible and contemplated to improve potency of therapeutic application over that of intravenous injection, oral ingestion, or other non-direct ingestion due to system-wide dissipation through intra-venous loss, gastro-intestinal breakdown or other physiologic breakdown or attrition mechanisms involved in non-site specific delivery of therapy. It is also possible and contemplated to provide a minimally invasive surgical enhancement technique to improve tissue responses without the requirement of long-term high dosage post-surgical treatment. It is further possible and contemplated to enable the clear and unambiguous determination of tissue temperatures when receiving energy from externally communicating devices, such as electrosurgical devices. Finally, it is possible and contemplated to enable the use of new surgical approaches that combine engineered irrigants for gene therapies that provide regenerative healing properties for specific tissues simultaneously with surgery, thereby limiting side effects to the patient.

The preceding examples can be repeated with similar success by substituting the generically or specifically described reactants and/or operating conditions of this invention for those used in the preceding examples.

Although the invention has been described in detail with particular reference to these preferred embodiments, other embodiments can achieve the same results. Variations and modifications of the present invention will be obvious to those skilled in the art and it is intended to cover in the appended claims all such modifications and equivalents. The entire disclosures of all references, applications, patents, and publications cited above are hereby incorporated by reference.

What is claimed is:

1. A solution for use in irrigation of surgical treatment sites during surgery, the solution comprising:
    an isotonic and buffered component; and
    at least one engineered irrigant component, wherein the engineered irrigant is a thermally responsive component that is useful in detecting the temperature of the surgical treatment site during surgery wherein the thermally responsive component effects a color or fluorescence change in response to a temperature change.

* * * * *